United States Patent
Podhajsky et al.

(10) Patent No.: US 8,002,462 B2
(45) Date of Patent: Aug. 23, 2011

(54) PORTABLE THERMALLY PROFILING PHANTOM AND METHOD OF USING THE SAME

(75) Inventors: Ronald J. Podhajsky, Boulder, CO (US); Arlan J. Reschke, Longmont, CO (US); Anna Belous, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 873 days.

(21) Appl. No.: 11/520,171

(22) Filed: Sep. 13, 2006

(65) Prior Publication Data
US 2008/0123716 A1    May 29, 2008

(51) Int. Cl.
*A61F 2/00* (2006.01)
*G01K 3/00* (2006.01)

(52) U.S. Cl. ......... 374/137; 607/100; 607/101; 607/102

(58) Field of Classification Search .......... 607/100–102; 374/137, E11.018, E3.001; 606/33, 41
See application file for complete search history.

(56) References Cited

U.S. PATENT DOCUMENTS

| | | | |
|---|---|---|---|
| 5,417,210 A * | 5/1995 | Funda et al. | 600/425 |
| 6,175,768 B1 * | 1/2001 | Arndt et al. | 607/101 |
| 6,375,606 B1 * | 4/2002 | Garibaldi et al. | 600/12 |
| 6,603,994 B2 * | 8/2003 | Wallace et al. | 600/434 |
| 6,625,482 B1 * | 9/2003 | Panescu et al. | 600/424 |
| 6,725,080 B2 * | 4/2004 | Melkent et al. | 600/424 |
| 6,725,482 B2 * | 4/2004 | George, II | 5/652 |
| 6,725,606 B2 * | 4/2004 | Nishikawa et al. | 49/502 |
| 6,994,704 B2 * | 2/2006 | Qin et al. | 606/34 |
| 2002/0091427 A1 * | 7/2002 | Rappaport et al. | 607/101 |
| 2003/0097130 A1 * | 5/2003 | Muller et al. | 606/41 |
| 2003/0103548 A1 * | 6/2003 | Prasad et al. | 374/44 |
| 2004/0097805 A1 * | 5/2004 | Verard et al. | 600/428 |
| 2004/0168692 A1 * | 9/2004 | Fogarty et al. | 128/899 |
| 2005/0220674 A1 * | 10/2005 | Shafirstein et al. | 422/99 |
| 2006/0042117 A1 * | 3/2006 | Winter et al. | 34/372 |
| 2007/0049915 A1 * | 3/2007 | Haemmerich et al. | 606/41 |
| 2009/0054887 A1 * | 2/2009 | Podhajsky | 606/33 |

FOREIGN PATENT DOCUMENTS

WO    WO 2006/042117 A2    4/2006

OTHER PUBLICATIONS

The Vibratome Company. "Operating Instructions Vibratome Series 5000-Brain Slice Chamber System". Accessed: Sep. 13, 2009. Published: Jan. 29, 2003 <http://web.archive.org/web/20030129194816/http://vibratome.com/global/manuals/VB5000Manual.PDF>.*

Goldberg, S. "Radiofrequency tumor ablation: princles and techniques". European Journal of Ultrasound. vol. 13, Issue 2, Jun. 2001. pp. 129-147.*

(Continued)

*Primary Examiner* — Lisa M Caputo
*Assistant Examiner* — Jonathan Dunlap (57) ABSTRACT

The present disclosure relates to thermal profiling systems for hypothermic and/or ablative energy systems and methods of their use. According to an aspect of the present disclosure, a system for profiling a thermal or electromagnetic treatment system, including an energy delivery probe, is provided. The profiling system includes a bath including a fitting supported on a side wall thereof configured for selective insertion of a distal tip of probe therethrough; a test gel disposed within the bath; and at least one piece of a reactive medium submerged in the test gel.

19 Claims, 7 Drawing Sheets

OTHER PUBLICATIONS

HydroFlex, Inc. "Flat or Dome Lens Ports". Accessed: Sep. 13, 2009. Published: Nov. 17, 2003 <http://hydroflex.com/site/helphints/flatdome.html>.*

Wonell et al. "Evaluation of Microwave and Radio Frequency Catheter Ablation in a Myocardium-Equivalent Phantom Model", IEEE Transactions on Biomedical Engineering, No. 10, Oct. 1992. <http://ieeexplore.ieee.org/stamp/stamp.jsp?arnumber=00161341>.*

Wonell et al. "Evaluation of Microwave and Radio Frequency Catheter Ablation in a Myocardium-Equivalent Phantom Model". IEEE Transactions on Biomedical Engineering, No. 10, Oct. 1992. <http://ieeexplore.ieee.org/stamp/stamp.jsp?arnumber=00161341>.*

* cited by examiner

PORTABLE THERMALLY PROFILING PHANTOM AND METHOD OF USING THE SAME

BACKGROUND

1. Technical Field

The present disclosure relates to energy delivery systems and, more particularly to thermal profiling systems for radiofrequency ("RF") and/or microwave energy systems and methods of their use.

2. Background of Related Art

The use of radiofrequency energy ("RF energy") and, in particular, radiofrequency electrodes ("RF electrodes") for ablation of tissue in the body or for the treatment of pain is known. Generally, such RF electrodes (e.g., probes, resistive heating elements and the like) include an elongated cylindrical configuration for insertion into the body to target tissue which is to be treated or ablated. The RF electrodes can further include an exposed conductive tip portion and an insulated portion. The RF electrodes can also include a method of internal cooling (e.g., a cool-tip or the like). Accordingly, when the RF electrode is connected to an external source of radiofrequency power (e.g., an electrosurgical generator), and current is delivered to the RF electrode, heating of tissue occurs near and around the exposed conductive tip portion thereof, whereby therapeutic changes in the target tissue, near the conductive tip, are created by the elevation of temperature of the tissue.

In some applications, for example, tumor ablation procedures, multiple electrodes are inserted into the body in an array to enlarge ablation volumes.

In a particular application, arrays of high frequency electrodes are inserted into tumors. The electrodes are typically placed in a dispersed fashion throughout the tumor volume to cover the tumor volume with uniform heat. The electrodes may be sequentially applied with high frequency voltage so that each electrode heats in sequence its neighboring tissue and then shuts off. Then, the next electrode does the same in a time series. This sequence of cycling the voltage through the electrodes continues at a prescribed frequency and for a period of time.

The electrode systems discussed above are limited by the practical size of lesion volumes they produce. Accordingly, electrodes with cooled conductive tips have been proposed. With cooling, radiofrequency electrode tips generally produce larger lesion volumes compared with radiofrequency electrodes, which are not cooled. For example, standard single cylindrical electrodes, with cooled tips, as described above, may make lesion volumes up to 3 to 4 cm in diameter in living tissue (e.g., the liver) by using cannulae of 1 to 2 mm in diameter and having exposed tip lengths of several centimeters.

SUMMARY

The present disclosure relates to thermal profiling systems for radiofrequency ("RF") energy systems and methods of their use.

According to an aspect of the present disclosure, a system for profiling a thermal or electromagnetic treatment system, including an energy delivery probe, is provided. The profiling system includes a bath including a fitting supported on a side wall thereof configured for selective insertion of a distal tip of probe therethrough; a test gel disposed within the bath; and at least one piece of a reactive medium submerged in the test gel.

The fitting may be a luer-type fitting.

The profiling system may include a ground ring disposed within the bath and a ground connection supported on the bath and electrically connected to the ground ring. The ground connection may be electrically connectable to an electrosurgical generator. The ground ring may have a shape substantially similar to a shape of the bath.

The profiling system may further include a shelf extending from an inner surface of a wall of the bath for supporting at least a portion of the reactive medium thereon when the reactive medium is in the bath. The profiling system may still further include at least one support rod disposed within the bath and configured to support at least a portion of the reactive medium when the reactive medium is in the bath.

The profiling system may include a cover configured to overlie the bath. The cover may have a concave profile. At least a central portion of the cover may extend into the test gel.

The profiling system may further include an image/data acquisition system for recording at least one of visual changes in the reactive medium, a configuration of the energy delivery probe, and a setting of an electrosurgical generator connected to the energy delivery probe.

According to another aspect of the present disclosure, a method of profiling a thermal treatment system, including an electrosurgical generator and at least one energy delivery probe connected to the electrosurgical generator, is provided. The method includes the steps of energizing an energy delivery probe in close proximity to a thermally reactive medium; and recording at least one of visual changes in the reactive medium, a configuration of the energy delivery probe, and a setting of the electrosurgical generator.

The method may further include the step of placing the thermally reactive medium in a test gel. The method may still further include the steps of introducing a distal end of the energy delivery probe into the test gel at a location above the reactive medium.

The method may include the step of placing the test gel in a bath and covering the bath with a concave cover. The method may also include the step of grounding the bath.

The method may further include the step of recording with an image/data acquisition system.

The step of profiling a reactive media may be repeated with a plurality of reactive media one each for each configuration of the energy delivery probe and/or each setting of the electrosurgical generator.

The method may further include the step of setting the temperature of the test gel to a predetermined temperature.

These and other aspects and advantages of the disclosure will become apparent from the following detailed description and the accompanying drawings, which illustrate by way of example the features of the disclosure.

BRIEF DESCRIPTION OF THE DRAWINGS

The features of the system and method of use of the system of the present disclosure will become more readily apparent and may be better understood by referring to the following detailed descriptions of illustrative embodiments of the present disclosure, taken in conjunction with the accompanying drawings, wherein.

DETAILED DESCRIPTION OF EMBODIMENTS

The systems and methods of the present disclosure provide for a more precise controlled positioning of a thermal probe in a cancer tumor targeted for treatment. Moreover, the systems and methods of the present disclosure provide for an improved ability to predict and/or visualize the depth and volume of treatment possible by the thermal probe when set to various operative parameters.

It will be readily apparent to a person skilled in the art that the systems and methods of use of the systems can be used to treat/destroy body tissues in any body cavity or tissue locations that are accessible by percutaneous or endoscopic catheters or open surgical techniques, and is not limited to cancer tumors. Applications of the systems and methods in all of these organs and tissues are intended to be included within the scope of the present disclosure.

1. System for Thermal Treatment

In the drawings and in the description which follows, the term "proximal", as is traditional, will refer to the end of the system, or component thereof, which is closest to the operator, and the term "distal" will refer to the end of the system, or component thereof, which is more remote from the operator.

Figure 1:
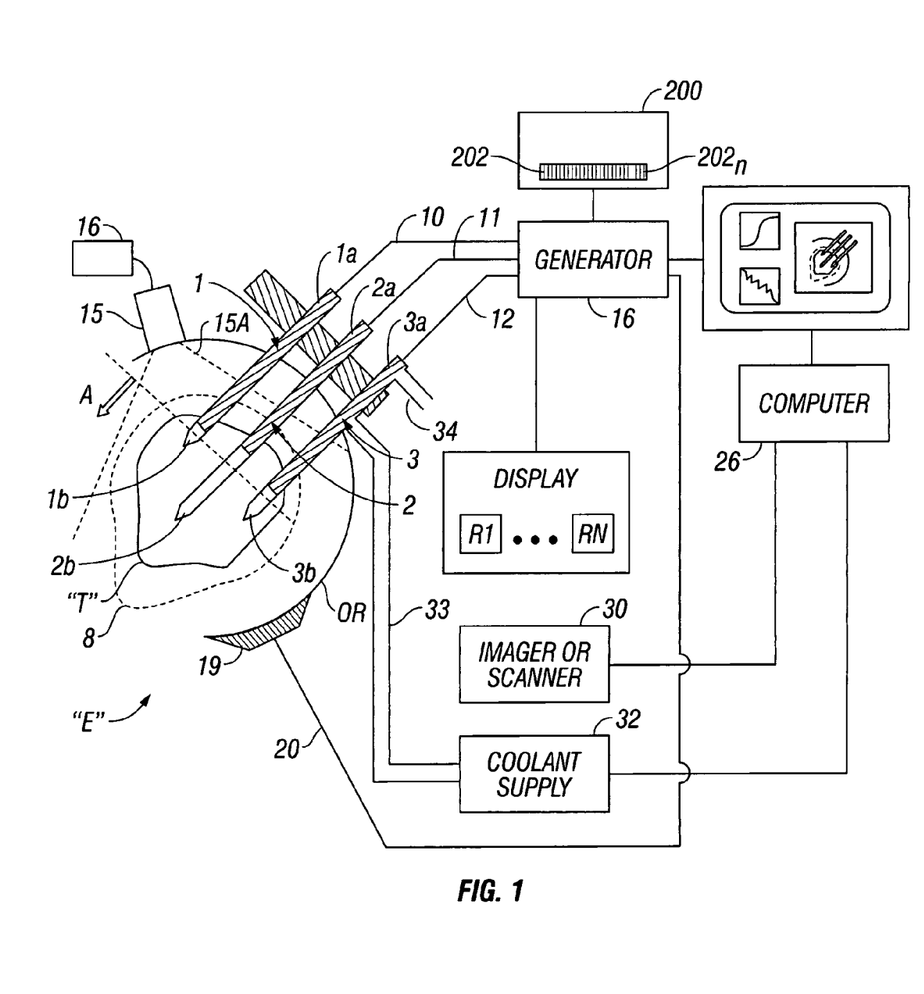
FIG. 1 is a schematic illustration of an ablation electrode array system multiple radiofrequency electrode probes being positioned in a patient's organ for producing heat ablation of a targeted tissue area.

With reference to FIG. 1, an electrode array system "E" may include a plurality of electrode probes 1, 2 and 3, which are to be inserted into an organ "OR" of a human body or any other body tissue, connectable to an electrosurgical generator 16 in order to perform tissue ablation and the like.

Each electrode probe 1, 2 and 3 includes a rigid shaft 1a, 2a and 3a, respectively, which enables electrodes 1, 2 and 3 to be easily urged into the body tissue or organ "OR". Each electrode probe 1, 2 and 3 terminates at a pointed distal tip 1b, 2b and 3b, respectively. A portion of the external surface of each electrode probe 1, 2 and 3 is covered with an insulating material, as indicated by hatched line areas in FIG. 1. Distal tips 1b, 2b and 3b are connected, through respective shafts 1a, 2a and 3a to cables 10, 11 and 12, respectively, and thereby to electrosurgical generator 16.

Electrode system "E" further includes a reference electrode 19, which may be placed in contact with the skin of a patient or an external surface of organ "OR" with a connection 20 to electrosurgical generator 16. Reference electrode 19 and connection 20 serves as a path for return current from electrosurgical generator 16 through electrode probes 1, 2 and 3.

As seen in FIG. 1, by way of illustration only, a targeted region to be ablated is represented in sectional view by the line "T". It is desired to ablate the targeted region "T" by fully engulfing targeted region "T" in a volume of lethal heat elevation. The targeted region "T" may be, for example, a tumor which has been detected by an image scanner 30. For example, CT, MRI, or ultrasonic image scanners may be used, and the image data transferred to a computer 26. As an alternate example, an ultrasonic scanner head 15 may be disposed in contact with organ "OR" to provide an image illustrated by lines 15A.

For example, in FIG. 1, dashed line 8 represents the ablation isotherm in a sectional view through organ "OR". Such an ablation isotherm may be that of the surface achieving possible temperatures of approximately 50° C. or greater. At that temperature range, sustained for approximately 30 seconds to approximately several minutes, tissue cells will be ablated. The shape and size of the ablation volume, as illustrated by dashed line 8, may accordingly be controlled by the configuration of the electrode array, the geometry of the distal tips 1b, 2b and 3b of electrode probes 1, 2 and 3, respectively, the amount of RF power applied, the time duration that the power is applied, cooling of the electrodes, etc.

A data processor 26 may be connected to the display devices to visualize targeted region "T" and/or ablation volume 8 in real time during the ablation procedure.

As seen in FIG. 1, electrode system "E" further includes a library 200 including a plurality of thermal profiles/overlays $202_n$. As used herein, the term library is understood to include and is not limited to repository, databank, database, cache, storage unit and the like. Each overlay 202 includes a thermal profile which is characteristic of and/or specific to a particular configuration of cannula/electrode assembly or amount of exposure (i.e., specific to the amount of electrode probe 1 extending from the distal tip of a cannula or the length of exposed distal tip 1b) of the cannula/electrode assembly. In addition, for each amount of exposure or configuration of the cannula/electrode assembly, a plurality of overlays $202_n$ is provided which includes a thermal profile which relates to, for example, the amount of time electrode probe 1 is activated, to the temperature to which electrode probe 1 is heated, etc.

Figure 2:
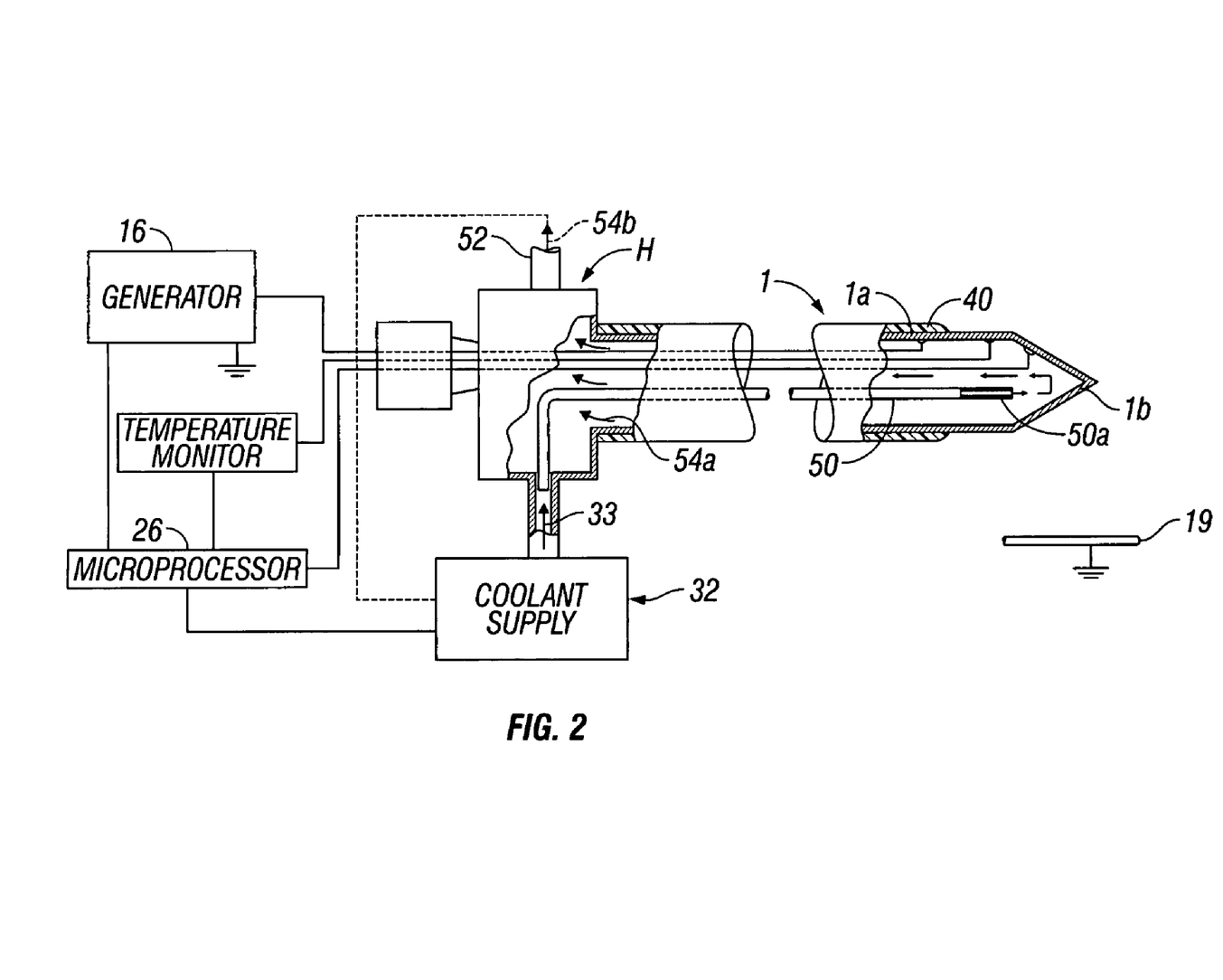
FIG. 2 is a broken-away partial cross-sectional view of a tip an electrode probe of FIG. 1.
Figure 3:
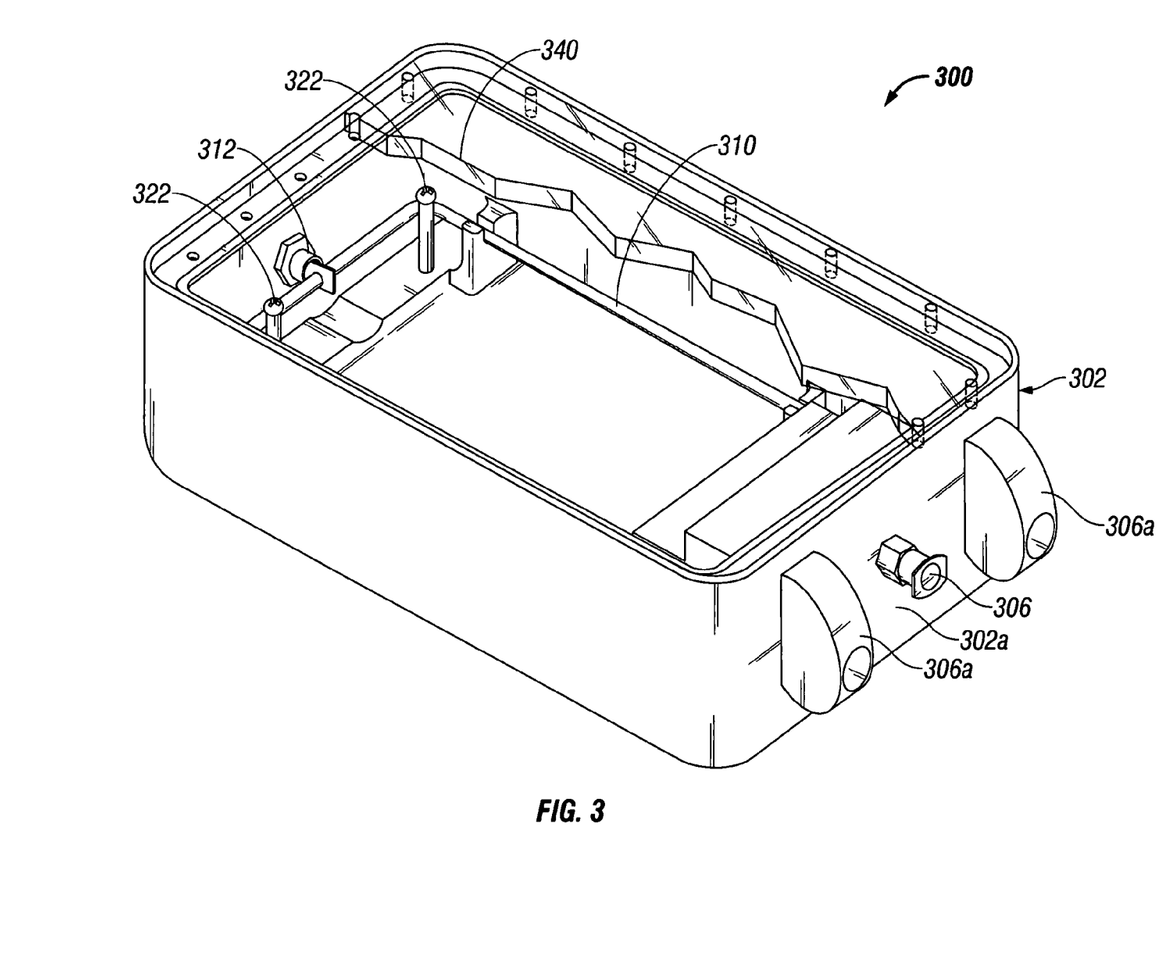
FIG. 3 is a rear, perspective view, partially broken-away, of a thermal profiling system according to an embodiment of the present disclosure.
Figure 4:
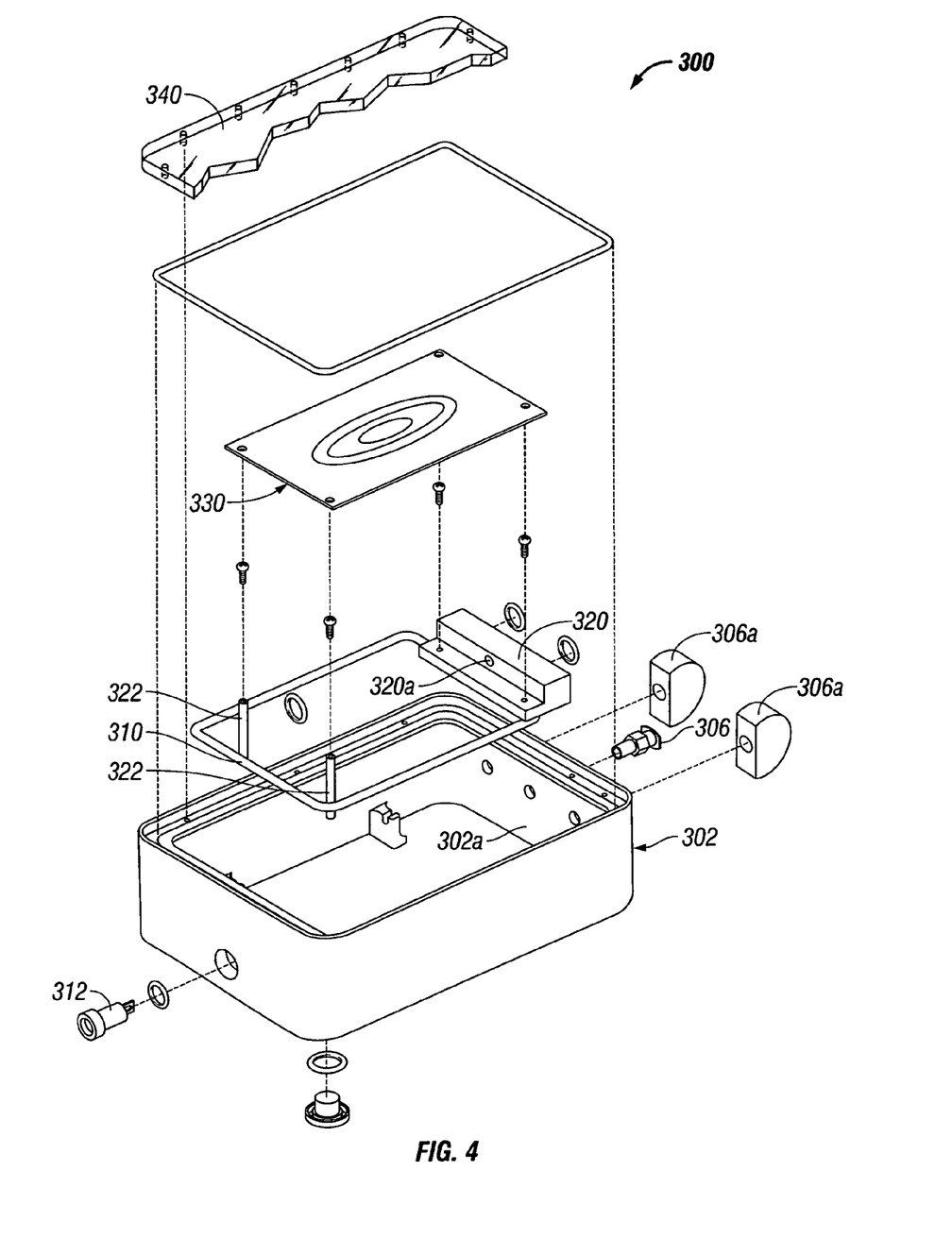
FIG. 4 is an exploded perspective view of the thermal profiling system of FIG. 3.
Figure 5:
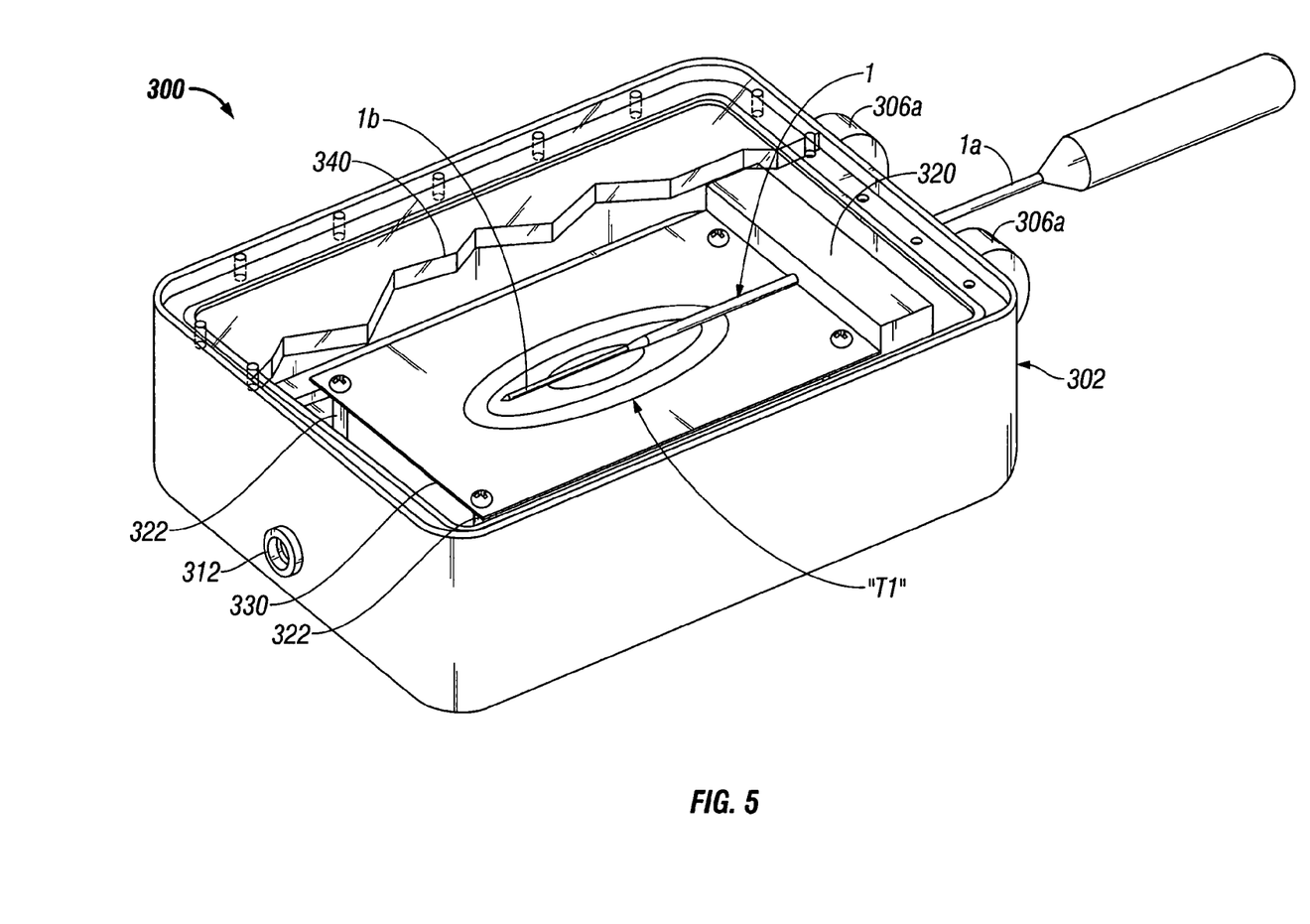
FIG. 5 is a front, perspective view, partially broken-away, of the thermal profiling system of FIGS. 3 and 4, illustrating the electrode of FIGS. 1 and 2 operatively associated therewith.
Figure 6:
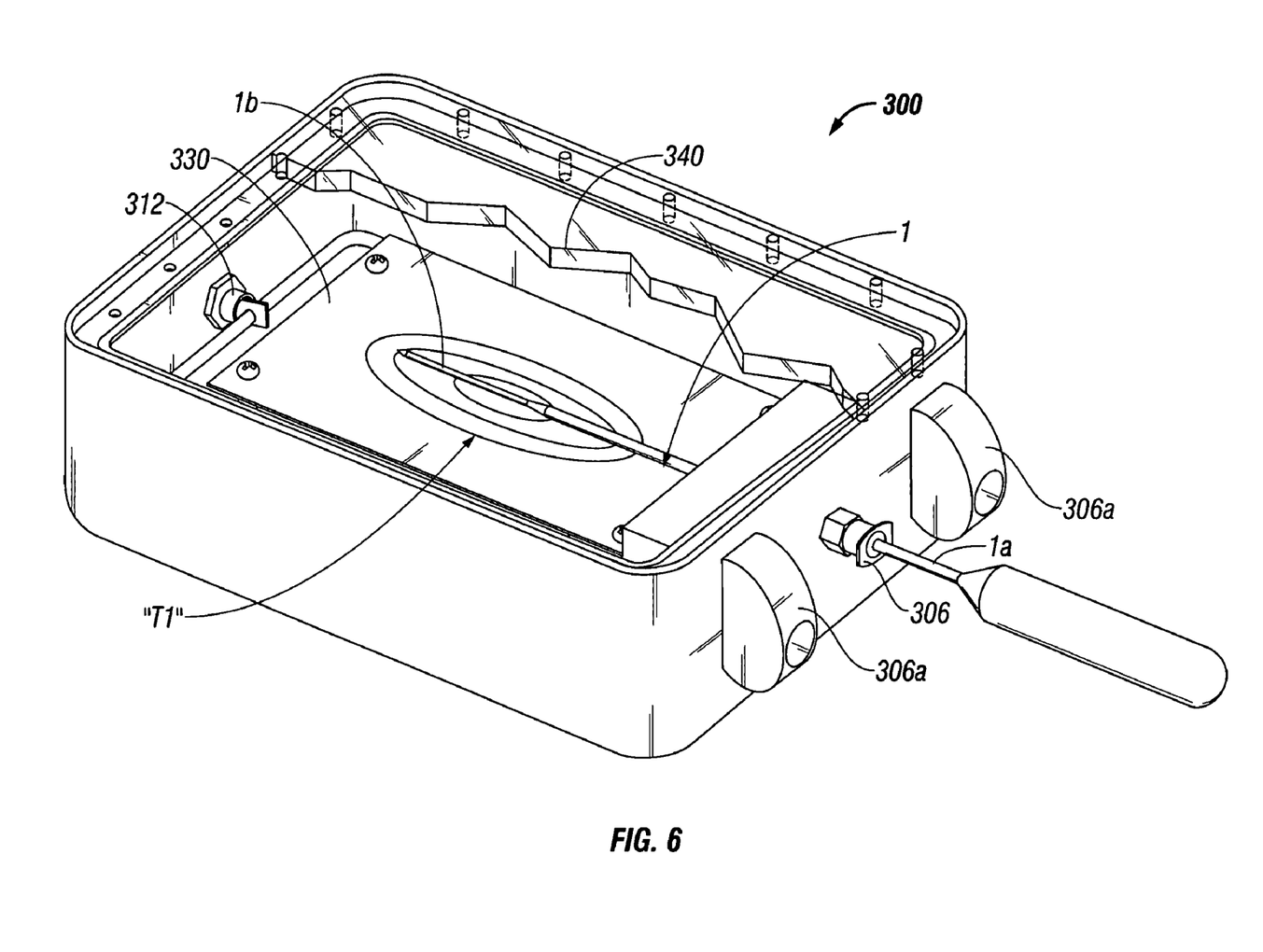
FIG. 6 is a rear, perspective view, partially broken-away, of the thermal profiling system of FIGS. 3 and 4, illustrating the electrode of FIGS. 1 and 2 operatively associated therewith.

As seen in FIG. 2, each electrode probe 1 includes a non-exposed proximal shaft 1a that is surrounded by an insulating material 40, and a non-insulated distal tip 1b exposed for DC or AC, preferably RF delivery. At its proximal end, electrode probe 1 is typically integrally associated with a hub "H" that carries electrical and coolant connections to electrode probe 1, as explained in greater detail below.

Temperatures at, or near distal tip 1b of electrode probe 1 may be controlled by adjusting a flow of fluid coolant through electrode probe 1. Accordingly, the temperature of the tissue contacting at or near distal tip 1b is controlled. In operation, fluid from a coolant supply 32 is carried the length of electrode probe 1 through a tube 50 extending from hub "H" to the distal end of electrode probe 1 terminating in an open end 50a at distal tip 1b. At the opposite end of electrode probe 1, within hub "H", tube 50 is connected to receive fluid. Backflow from distal tip 1b is through an exit port 52 of hub "H" as illustrated by arrows 54a, 54b.

2. System for Profiling Thermal Treatment System

Turning now to FIGS. 3-7, a system for thermal profiling electrode system "E" is generally designated as 300. Thermal profiling system 300 includes a bath 302 containing a quantity of a transparent test gel 304 (see FIG. 7), e.g., electrically and thermally conductive polymer, hydrogel or other suitable clear conductive medium. Bath 302 may be fabricated from any suitable non-conductive material, such as, for example, polycarbonate, plastic and the like.

Profiling system 300 further includes a fixture or fitting 306 extending through a side wall 302a of bath 302 and being configured and adapted to selectively receive an electrode probe 1 therethrough. Fitting 306 is configured to inhibit leakage of test gel 304 from within bath 302 when no electrode probe 1 is inserted therein and to form a substantially fluid tight seal around electrode probe 1 when electrode probe 1 is inserted therethrough. Fitting 306 may be a single use fitting which is replaceable after each use or after several uses. Fitting 306 may include and is not limited to a luer-type fitting, a pierceable membrane port, and the like. Guards 306a may be placed at least on opposite sides of fitting 306 to prevent inadvertent contact or disruption of fitting 306. Any number of fittings may be provided in a side wall 302a of bath 302 in order to accommodate multiple electrode probes.

Profiling system 300 further includes a ground ring 310 disposed within bath 302. Ground ring 310 is fabricated from a suitable conductive material and functions to receive and/or transmit RF energy from/to electrode probe 1 during operation of profiling system 300. In one embodiment, as seen in FIGS. 3-6, ground ring 310 is shaped to substantially complement the shape of bath 302 so as to extend substantially around an inner perimeter of bath 302. A ground connection 312 is provided that extends through a wall of bath 302 and electrically connects to ground ring 310. Ground connection 312 is used to electrically connect ground ring 310 to an electrosurgical generator, such as electrosurgical generator 16.

In the event that electrode probe 1 is energized with a microwave generator, ground ring 310 may be removed in order to reduce any reflected energy that may be caused by the presence of ground ring 310.

In one embodiment, profiling system 300 may include a shelf 320 supported on and extending from an inner surface of a wall of bath 302, and at least one support rod 322 extending upwardly into bath 302 from a lower surface thereof. Shelf 320 and support rods 322 function to support a sheet of thermally sensitive/reactive paper film or medium 330 within bath 302. Shelf 320 and support rods 322 are configured such that reactive medium 330 is maintained in a substantially parallel plane to a lower surface of bath 302 when reactive medium 330 is placed within bath 302.

Profiling system 300 further includes at least one sheet of suitable thermally sensitive/reactive paper film or medium 330. For example, thermally reactive medium 330 may include liquid crystal (LC) thermometry paper. A plurality of sheets of thermally reactive medium 330 may be provided to create a respective, unique and distinct thermal profile thereon for each individual characteristic of treatment system 100 or parameter/setting of treatment system 100.

Figure 7:
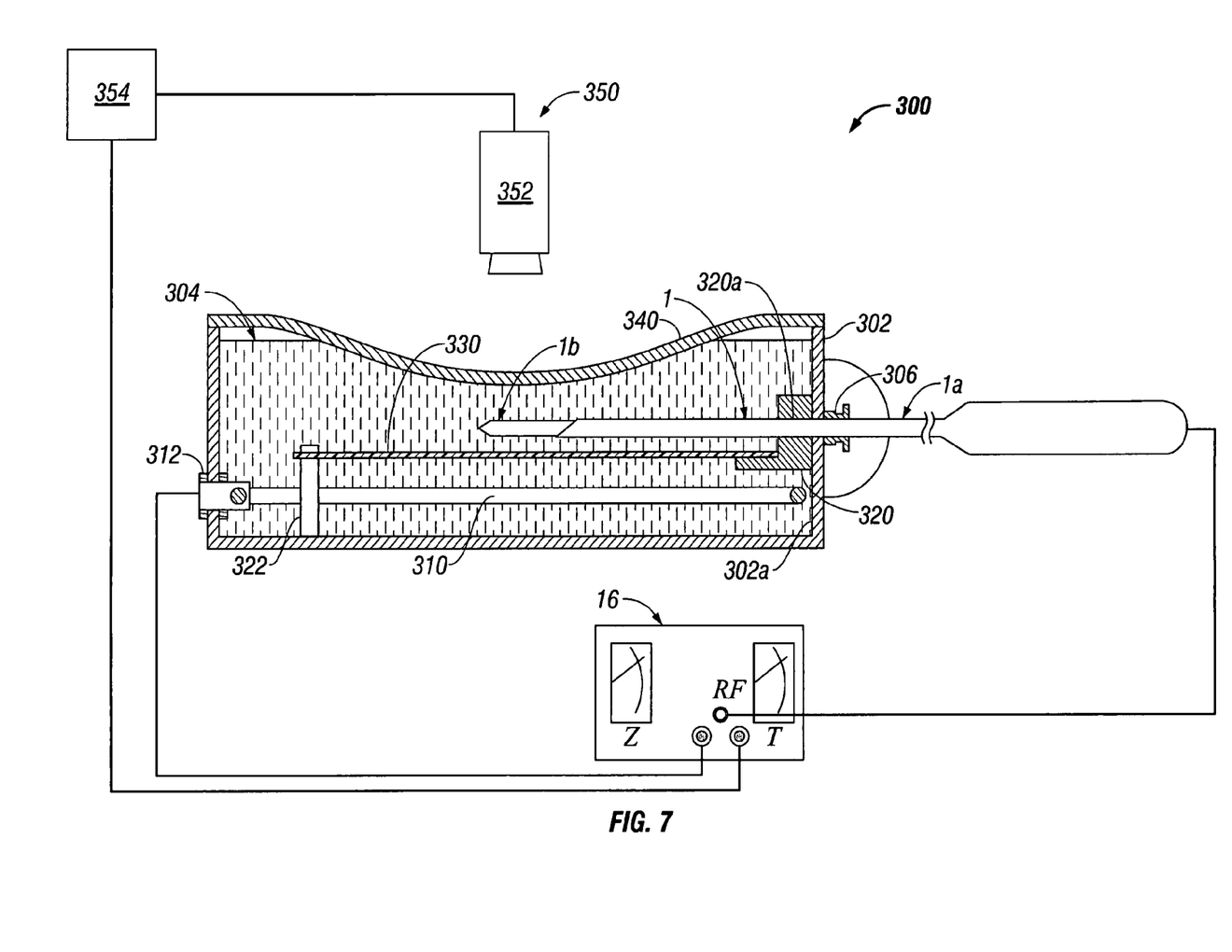
FIG. 7 is a schematic, longitudinal cross-sectional view of the thermal profiling system of FIGS. 3-6, as taken through 7-7 of FIG. 5.

Profiling system 300 further includes a cover 340 configured to selectively overlie bath 302. Cover 340 may be fabricated from any suitable transparent or clear material, such as, for example, glass, polyacrylic, polycarbonate, etc. Cover 340 may be secured to a top edge of bath 302 by any suitable fastening element, such as, for example, screws, clips, hinges and the like. In one embodiment, as seen in FIG. 7, cover 340 may have a generally concave profile (i.e., cover 340 extends into bath 302 when properly secured thereto) such that cover 340 extends into test gel 304. In this manner, during operation of profiling system 300, in the event of any bubble production or creation, said bubbles will tend to drift away from the center of bath 302 thus leaving the field of view to reactive medium 330 substantially free from obstruction.

As seen in FIG. 7, profiling system 300 may further include an image/data acquisition system 350 operatively associated with electrosurgical generator 106 and bath 302. For example, the image/data acquisition system 350 may include a camera 352 for recording at least one of the visual changes occurring in reactive medium 330 and the parameters of electrosurgical generator 106 (e.g., power settings, time settings, wave settings, duty-cycle settings, electrode probe 1 configuration, etc.). Image/data acquisition system 350 may also include a processor 354 connected between camera 352 and electrosurgical generator 16.

3. Method of Using Thermal Profiling System

With reference to FIGS. 1-7, a method of using thermal profiling system 300 to create at least one thermal profile for electrode system "E" is described. According to one method of the present disclosure, an un-used or new reactive medium 330 is submerged in bath 302 containing test gel 304 therein. Reactive medium 330 is placed within bath 302 in such a manner that a color changing side of reactive medium 330 is facing cover 340 or away from a bottom of bath 302. Reactive medium 330 may be positioned within bath 302 such that at least a portion of reactive medium 330 is placed on shelf 320 and at least a portion of reactive medium 330 is placed on supports 322. In one embodiment, fasteners, such as screws, may be used to secure reactive medium 330 to shelf 320 and supports 322. With reactive medium 330 disposed within test gel 304 within bath 302, cover 340 is placed on bath 302 thereby closing off bath 302.

Electrode probe 1 is then introduced into bath 302 by penetrating a distal tip 1b thereof through fitting 306 and advancing electrode probe 1 through fitting 306 until the distal tip of electrode probe 1 is located substantially at the center of reactive medium 330. The distal tip 1b of electrode probe 1 may be positioned substantially near the center of reactive medium 330. Distal tip 1b of electrode probe 1 is spaced a distance from reactive medium 330.

Shelf 320 may include a passage or lumen 320a formed therethrough that is aligned with fitting 306 when shelf is secured to bath 302. Lumen 320a aides in maintaining electrode probe 1 orthogonal with respect to side wall 302a and aids in preventing electrode 1 from pivoting with respect to fitting 306. In this manner, the distal tip of electrode probe 1 is better maintained near the center of reactive medium 330 and spaced a distance from reactive medium 330.

Electrode probe 1 is electrically connected to an active port or terminal of electrosurgical generator 16, and ground connection 312 of profiling system 300 is electrically connected to a return port or terminal of electrosurgical generator 16.

With electrode probe 1 set-up in bath 302, image/data acquisition system 350 may be activated to record any visual changes in reactive medium 330, the parameters of electrosurgical generator 16, and the configuration of electrode probe 1.

Electrosurgical generator 16 is then configured or set to a predetermined setting. For example, electrosurgical generator 16 is set to a predetermined temperature (e.g., about 42° C. or about 80° C., which are common pain treatment temperatures), a predetermined waveform, a predetermined duty cycle, a predetermined time period or duration of activation, etc.

Electrosurgical generator 16 is then activated such that RF energy or radiation communicated between the distal tip of electrode probe 1 and ground ring 310 effects reactive medium 330 to create a thermal image "T1" thereon.

The method may further include recording the thermal image "T1" with image/data acquisition system 350. In particular, the temperature gradients or "halos" created on reactive medium 330 may be recorded visually by camera 352 of the image/data acquisition system 350 and stored electronically in the processor 354. In particular, as the heat generated by electrode probe 1 stimulates reactive medium 330, the temperature gradients or "halos" area as colored rings or the like indicated areas of relatively higher temperature and areas of relatively lower temperature. It is contemplated that the particular reactive medium 330 used may be selected so as to display only a single temperature of interest as opposed to a range of temperatures.

Additionally, the image/data acquisition system 350 may record and store the settings and/or parameters of electrosurgical generator 16 (e.g., temperature, impedance, RF power, RF current, RF voltage, mode of operation, exposure of distal tip 1b of electrode probe 1, duration of application of the electrosurgical energy, etc.) associated with the creation of the image on reactive medium 330.

Following the creation of the image on reactive medium 330, electrosurgical generator 16 is turned off, electrode probe 1 may be withdrawn from bath 302, and used reactive medium 330 may be replaced with a new or un-used reactive medium 330. The process or method is repeated for a different set of parameters for electrosurgical generator 16 and/or electrode probe 1 configuration.

According tone method of the present disclosure, prior to activation of electrosurgical generator 16, a temperature of test gel 304 within bath 302 is stabilized to a temperature of approximately 37° C.

While the method disclosed herein contemplates positioning of reactive medium 330 in an orientation substantially parallel to a bottom surface of bath 302, it is envisioned and within the scope of the present disclosure to position reactive medium 330 in bath 302 at any desired orientation in order to provide the thermal information of interest.

The images created on the reactive media 330 and the associated electrosurgical generator parameters and electrode probe 1 configuration may be compared to one another in order to evaluate the performance of different electrodes and different electrosurgical generators.

Additionally, the images created and information recorded may be used by the clinician in order to better visualize and understand how to achieve more optimized results during thermal treatment of tissue, such as, for example, ablation of tissue, tumors and cancer cells.

During activation of electrosurgical generator 16 and heating of the distal tip of electrode probe 1, an air bubble may be formed at the distal tip. Accordingly, by providing a cover 340 having a substantially concave profile, the bubble created with would be displaced away from the viewing area. In order to do so, the concavity of cover 340 must extend into test gel 304.

Bath 302 may have any shape and/or configuration desired. While a generally rectangular bath 302 has been shown, it is envisioned that bath 302 may have a more organic shape, such as, for example, circular, ovular, kidney-shaped, liver-shaped, lung shaped, etc. Accordingly, a clinician may better visualize and the potential effects of thermal treatment on a patient prior to actually performing the treatment procedure.

The reactive medium 330 may have any shape and/or configuration desired. While a general rectangular reactive medium has been shown, it is envisioned that reactive medium 330 may have a shape that conforms to the selected bath 302 shape or that the reactive medium 330 may be shaped to allow circulation of the heated test gel 304. The reactive medium may have holes perforating its body including slots, slits, gratings, etc.

While the above described thermal profiling system has been specifically described in relation to use with an RF energy system and electrode probe, it is understood and within the scope of the present disclosure for the thermal profiling system to be used in conjunction with any suitable hypothermic and/or ablative energy system including, for example, microwave energy systems employing microwave antennas for delivering ablative energy.

The above described thermal profiling system has been specifically described in relation to the profiling of a single electrode probe at a given time. However, it is envisioned and within the scope of the present disclosure for multiple electrode probes, e.g., two or more, to be introduced into the test gel and for image/data to be acquired thereof, in accordance with the method described above.

Reference may be made to International Application Serial No. PCT/US2005/036168, filed on Oct. 5, 2005, the entire content of which is incorporated herein by reference, for exemplary methods of using the images and/or data acquired from image/data acquisition system 350 in the assistance and/or performance of surgical procedures and the like.

While the above description contains many specific examples, these specific should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A system for profiling a thermal or electromagnetic treatment system including an energy delivery probe, the profiling system comprising:
    a bath including a fitting supported on a side wall thereof configured for selective insertion of a distal tip of probe therethrough;
    a test gel disposed within the bath; and
    at least one piece of a reactive medium submerged in the test gel and supported above a bottom surface of the bath,
    wherein the energy delivery probe is submerged in the test gel in a substantially parallel orientation with respect to a top surface of the at least one piece of reactive medium such that the energy delivery probe is positionable about a center of the at least one piece of reactive medium when the energy delivery probe is secured to the bath.

2. The profiling system according to claim 1, wherein the fitting is a luer-type fitting.

3. The profiling system according to claim 1, further comprising a ground ring disposed within the bath.

4. The profiling system according to claim 3, further comprising a ground connection supported on the bath and electrically connected to the ground ring, wherein the ground connection is electrically connectable to an electrosurgical generator.

5. The profiling system according to claim 3, wherein the ground ring has a shape substantially similar to a shape of the bath.

6. The profiling system according to claim 1, further comprising a shelf extending from an inner surface of a wall of the bath for supporting at least a portion of the reactive medium thereon when the reactive medium is in the bath.

7. The profiling system according to claim 6, further comprising at least one support rod disposed within the bath and configured to support at least a portion of the reactive medium when the reactive medium is in the bath.

8. The profiling system according to claim 1, further comprising a cover configured to overlie the bath.

9. The profiling system according to claim 8, wherein the cover is concave.

10. The profiling system according to claim 9, wherein at least a central portion of the cover extends into the test gel.

11. The profiling system according to claim 1, further comprising an image/data acquisition system for recording at least one of visual changes in the reactive medium, a configuration of the energy delivery probe, and a setting of an electrosurgical generator connected to the energy delivery probe.

12. A method of profiling a thermal treatment system including an electrosurgical generator and at least one energy delivery probe connected to the electrosurgical generator, the method includes the steps of:

providing a bath with a test gel therein;

placing a thermally reactive medium in the bath such that the thermally reactive medium is submerged in the test gel;

positioning an energy delivery probe in the bath of test gel in close proximity to the thermally reactive medium such that the energy delivery probe and the thermally reactive medium are in a spaced-apart relation with respect to each other with a volume of test gel disposed therebetween, wherein the energy delivery probe is submerged in the test gel in a substantially parallel orientation with respect to a top surface of the at least one piece of reactive medium such that the energy delivery probe is positionable about a center of the at least one piece of reactive medium when the energy delivery probe is secured to the bath;

energizing the energy delivery probe; and recording at least one of visual changes in the reactive medium, a configuration of the energy delivery probe, and a setting of the electrosurgical generator.

13. The method according to claim 12, wherein the test gel in the bath is standing still.

14. The method according to claim 13, further comprising the step of positioning a distal end of the energy delivery probe in the test gel at a location above the reactive medium.

15. The method according to claim 13, further comprising the step of covering the bath with a concave cover.

16. The method according to claim 15, further comprising the step of grounding the bath.

17. The method according to claim 13, further comprising the step of setting the temperature of the test gel to a predetermined temperature.

18. The method according to claim 12, further comprising the step of recording with an image/data acquisition system.

19. The method according to claim 12, further comprising the step of profiling a plurality of reactive media each having a unique one of a configuration of the energy delivery probe and a setting of the electrosurgical generator.

\* \* \* \* \*